(12) United States Patent
Dobrokhotov et al.

(10) Patent No.: US 10,132,769 B2
(45) Date of Patent: Nov. 20, 2018

(54) DOPED, METAL OXIDE-BASED CHEMICAL SENSORS

(71) Applicant: VAON, LLC, Bowling Green, KY (US)

(72) Inventors: Vladimir Dobrokhotov, Bowling Green, KY (US); Alexander Larin, Bowling Green, KY (US)

(73) Assignee: VAON, LLC, Bowling Green, KY (US)

( * ) Notice: Subject to any disclaimer, the term of this patent is extended or adjusted under 35 U.S.C. 154(b) by 0 days.

(21) Appl. No.: 15/649,602

(22) Filed: Jul. 13, 2017

(65) Prior Publication Data

US 2018/0017516 A1  Jan. 18, 2018

Related U.S. Application Data

(60) Provisional application No. 62/361,716, filed on Jul. 13, 2016.

(51) Int. Cl.
*G01N 27/12* (2006.01)
*H01L 29/24* (2006.01)

(52) U.S. Cl.
CPC ........... *G01N 27/125* (2013.01); *H01L 29/24* (2013.01); *G01N 27/128* (2013.01)

(58) Field of Classification Search
CPC ............................. G01N 27/125; H01L 29/24
See application file for complete search history.

(56) References Cited

U.S. PATENT DOCUMENTS

| | | | |
|---|---|---|---|
| 4,238,758 A | 12/1980 | Suzuki | |
| 4,338,281 A | 7/1982 | Treitinger et al. | |
| 4,399,684 A | 8/1983 | Advani et al. | |
| 4,453,151 A | 6/1984 | Leary et al. | |
| 4,542,640 A | 9/1985 | Clifford | |
| 4,847,783 A | 7/1989 | Grace et al. | |
| 5,250,170 A | 10/1993 | Yagawara et al. | |
| 5,605,612 A * | 2/1997 | Park | G01N 27/12 204/429 |
| 5,783,154 A | 7/1998 | Althainz et al. | |
| 6,235,243 B1 | 5/2001 | Fleischer et al. | |
| 7,406,856 B2 * | 8/2008 | Bottner | G01N 27/125 73/31.06 |
| 8,669,131 B1 * | 3/2014 | Smith | G01N 27/125 204/431 |
| 2003/0045017 A1 | 3/2003 | Kubena | |

(Continued)

FOREIGN PATENT DOCUMENTS

| | | | |
|---|---|---|---|
| GB | 2533294 | * 12/2014 | ............. G01N 27/12 |
| WO | 96/01992 | 1/1996 | |

OTHER PUBLICATIONS

The Karlsruhe Micro Nose, KAMINA, Application Note: 31052, 2008.

(Continued)

*Primary Examiner* — Thomas L Dickey
*Assistant Examiner* — Farid Khan
(74) *Attorney, Agent, or Firm* — Vance Intellectual Property, PC

(57) ABSTRACT

The present invention generally relates to doped, metal oxide-based sensors, wherein the doped-metal oxide is a monolayer, and platforms and integrated chemical sensors incorporating the same, methods of making the same, and methods of using the same.

19 Claims, 3 Drawing Sheets

■ $SiO_2$ (300 nm)
▫ Pt (300 nm)
■ Si (200 um)
■ $SnO_2/TiO_2$ dual oxide (30 nm)

(56) References Cited

U.S. PATENT DOCUMENTS

| | | | |
|---|---|---|---|
| 2006/0185420 A1* | 8/2006 | Nakagawa | G01N 27/125 73/31.06 |
| 2006/0196248 A1* | 9/2006 | Nakano | G01N 27/125 73/31.06 |
| 2009/0148347 A1* | 6/2009 | Lee | C04B 35/4682 422/83 |
| 2009/0159447 A1* | 6/2009 | Cui | G01N 27/125 204/431 |
| 2013/0140064 A1 | 6/2013 | Burberry et al. | |
| 2014/0138259 A1 | 5/2014 | Mickelson et al. | |

OTHER PUBLICATIONS

Goschnick, J. et al., Condition Monitoring for Intelligent Household Appliances, Sensors in Household Appliances 2002, 5, 52-68.
The Karlsruhe Micronose KAMINA: Novel technology for intelligent systems (brochure).
Arnold, C. et al., Air Quality Monitoring and Fire Detection with the Karlsruhe Electronic Micronose Kamina, IEEE Sensor Journal, Aug. 1-22, 2001.

\* cited by examiner

DOPED, METAL OXIDE-BASED CHEMICAL SENSORS

FIELD OF THE INVENTION

The present invention generally relates to doped, metal oxide-based sensors, wherein the doped-metal oxide is a monolayer, and platforms and integrated chemical sensors incorporating the same, methods of making the same, and methods of using the same.

BACKGROUND OF THE INVENTION

Chemiresistors (conductometric sensors) are traditionally used as building blocks for integrated chemical sensors (artificial olfactory systems, electronic noses). A chemiresistor is a device whose electrical resistance is modulated by molecular adsorption on its surface. The changes in resistance are proportional to the partial vapor pressure. Hence a chemiresistor converts the concentration of chemicals in the ambient air into a corresponding measurable electrical signal. A chemiresistor is constructed from a vapor-sensitive material placed between conducting leads. One of the best chemically sensitive materials ever discovered is nanoscale tin oxide ($SnO_2$). The sensing mechanism of metal oxides is primarily based on the activation of atmospheric oxygen on the semiconductor surface. Consequently, catalytic reactions of gaseous species with oxygen sites on the surface induce charge transfer from the surface to the bulk, i.e., subsurface, which changes the electrical resistance of the device.

Most conventional chemical sensors are based on recognition of particular analytes, e.g., methane, carbon monoxide, hydrogen sulfide, etc. For complex mixtures, however, this approach is not the most reliable, since it causes frequent false alarms due to cross-sensitivity of sensors to different analytes. The advantage of using integrated sensory systems (electronic noses) is in their ability to learn the chemical signatures of interest, similar to training of canines. Unlike many other analytical techniques, an integrated sensor does not try to separate all the chemical components within a sample, but it perceives a sample as a whole, creating a global fingerprint. For example, the smell that emanates from coffee has hundreds of different chemical components, but our biological olfactory system (and the integrated sensor) simply identifies the total chemical composition as coffee. In an integrated sensor, the headspace from a sample (i.e., the gases emanating from a sample) is delivered to an array of chemical sensors. As each sensor is different in some way (usually broadly tuned to a different chemical group), each sensor's response to a sample is different. These responses can then be used to form a chemical fingerprint of a sample. The response is seen as a change in electrical properties (normally resistance) of the sensor. Specialized software then identifies the sample from this fingerprint.

These sensors usually suffer more or less from cross sensitivity, i.e., apart from their response to a particular target gas they do (to a certain extent) respond to other gases as well. For instance, a methane sensor is also responsive to propane, butane, and natural gas in general. In this respect, a single output sensor cannot be sufficient, even if only one target gas is to be detected. However, a combination of several gas sensors, each providing a different sensitivity spectrum, a so-called sensor array, delivers signal patterns characteristic for the gases to which the array is exposed. These signal patterns enable the distinction between individual gases or gas ensembles. Which gases can or cannot be detected or distinguished depends on the sensor type and the extent of the difference in selectivity between the sensors. Now, the cross sensitivity of the individual sensors, due to a low selectivity even turns out to be an advantage. A low selectivity (in the case of a single sensor a disadvantage for detecting a particular gas), now allows the array to respond to a wide range of gases. A combination of several chemiresistors, each providing a different sensitivity spectrum, a so-called sensor array, delivers signal patterns characteristic for the gases to which the array is exposed.

For more than two decades now, small and simple gas sensors, which provide one output signal only, have been commercially available. Typically, they are manufactured by the sol-gel method, in which metal oxide layers are deposited in the form of a viscous paste and then baked in an inert environment, creating thick films. Metal oxide sensors from Figaro (TGS sensors) and Henan Hanwei Electronics Co., ltd. (MQ sensors) are manufactured by this method. The first integrated sensory systems equipped with arrays assembled from separate sensors were manufactures in the early 90s.

Individually manufactured sensors equipped with sockets are placed in plugs on a carrier plate of several centimeters in size. There are multiple drawbacks associated with this conventional design:

1. The sol-gel process utilized for manufacturing of individual sensors does not provide precise control over the oxide layer thickness. Because of that, variations from sensor to sensor in this manufacturing process are unavoidable. As a consequence, even if the datasheet provides a calibration curve, every sensor manufactured by the sol-gel method requires a calibration and verification by the consumer, using costly specially prepared gaseous mixtures.
2. Individual sensors in a sensor array evolve over time. This phenomenon is known as a long-term drift. For a conventional integrated system, individual elements evolve differently, causing failures of pattern recognition algorithms.
3. Short-term drift due to the fluctuations in the environment also has different effects on individual elements in a conventional integrated system and causes failures of pattern recognition algorithms.
4. Frequently, individual sensors in a conventional integrated system have variances in response time. This means that some of them respond to analyte exposure faster than the others. Upon exposure to analyte but before reaching a stationary state, sensors of integrated system go through the transient phase. If they are not well-synchronized, during the transient phase, the conventional integrated system typically reports several false results. Synchronization of individual elements of a conventional integrated system is another time consuming process, and has to be implemented for each unit after the assembly.
5. If one of the sensors in a conventional integrated system fails and needs to be replaced, the entire system will need to undergo synchronization and calibration.
6. The thickness of the metal oxide layer is a key parameter that determines sensor sensitivity. The thinner the layer—the higher the sensitivity. Since only the thick films can be produced by the sol-gel method, sensors formed with this method have limited sensitivity. For most chemical compounds, the sensitivity of a sol-gel sensor is unable to go below 1 ppm.
7. Sol-gel films, which are thick, have relatively long time of recovery after exposure, which can be up to 1 min for exposure to high concentrations.

8. Conventional integrated sensory systems are typically large in size. Discrimination power of an integrated sensor depends on the number of individual basic sensing elements with different chemiresistive properties. However, an increase in the number of sensors inevitably leads to an increase in size, which causes makes a non-uniform distribution of chemicals over the sensor array upon exposure to gaseous analyte.

9. As a consequence of their size, conventional integrated systems often require sophisticated gas sampling systems, splitting the analyte gas into identical fractions for each sensor.

10. Conventional integrated sensory systems typically have high power consumption (hundreds of watts).

11. Conventional integrated sensory systems typically have high manufacturing costs, especially in the case of an advanced sampling system. Synchronization and calibration also makes the manufacturing process time-consuming.

In view of the above, it would be advantageous to develop new chemiresistors and integrated chemical sensors and methods of making and using the same, which overcome at least some of the above-noted drawbacks with conventional integrated sensory systems.

SUMMARY OF THE INVENTION

In an aspect, the present invention provides novel, doped, metal oxide-based chemical sensors.

In an aspect, the present invention provides novel, doped, metal oxide-based chemical sensor platforms.

In an aspect, the present invention provides novel, doped, metal oxide-based integrated chemical sensors.

In another aspect, the present invention provides a novel method of making doped, metal oxide-based chemical sensors, platforms and/or integrated chemical sensors.

In another aspect, the present invention provides use of novel, doped, metal oxide-based chemical sensors, platforms, and/or integrated chemical sensors.

These and other aspects, which will become apparent during the following detailed description, have been achieved by the inventors' discovery of new doped, metal oxide-based chemical sensors; doped, metal oxide-based chemical sensor platforms; and, metal oxide-based integrated chemical sensors.

DETAILED DESCRIPTION OF THE INVENTION

Figure 1:
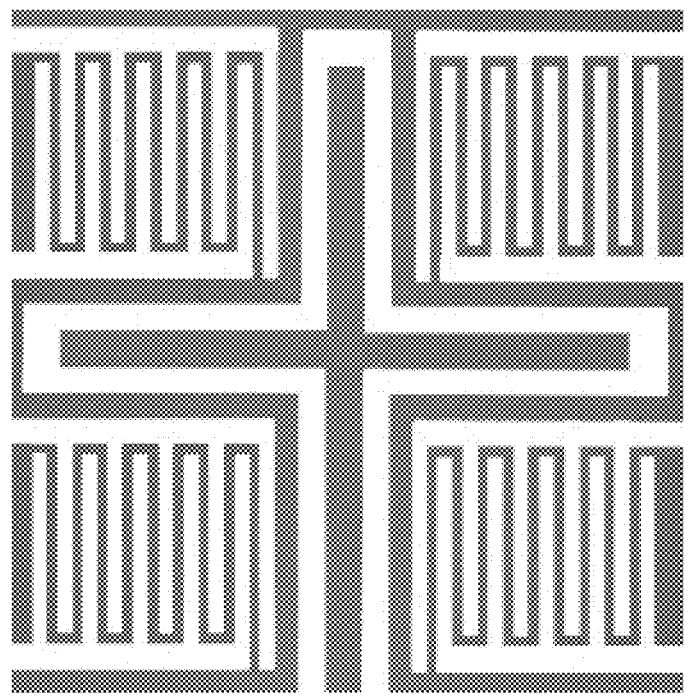
FIG. 1 shows a heating element (white area surrounding the green "T" in the middle) and electrical leads (interdigitated terminals)(remaining white area) deposited on a wafer (green).

In order to overcome the typical limitations of conventional integrated sensory systems, a new highly-integrated multisensory system and manufacturing technique was created. The newly developed manufacturing technique is simple, straight-forward, inexpensive, controllable, and repeatable.

In order to miniaturize the sensor and minimize power consumption, a design was developed that allows one to place multiple sensing elements on a single silicon chip. This "lab-on-a-chip" design utilizes an array of metal leads (e.g., platinum and gold), deposited on a silicon wafer using the stencil (shadow mask) method. Deposition of electrodes is followed by the deposition of catalytic, doped metal oxide layers. The multisensory system is wire-bonded to a multi-pin packaging platform for further integration in an electronic device.

For efficient recognition of analytes, each sensor of the integrated sensory system can be tuned to a certain chemical group (selective); hence each sensor's response to a gaseous species can be different. These responses can then be used to form a chemical fingerprint of an analyte. The discrimination power of the artificial olfactory system comes from the integrated signal from the entire array of sensors. Selectivity of each sensor in the array is defined as the ability to promote only the rate of desired chemical reaction and also retard the undesired reactions.

In an aspect, the present invention relates to a novel manufacturing technique that allows for tuning the catalytic selectivity of the sensors in the desired manner. This aspect of the invention is based on co-sputtering a metal oxide (e.g., $SnO_2$) with a dopant (e.g., a second oxide such as $TiO_2$ or $In_2O_3$)(or using another technique that provides fine control of layer thickness and repeatability).

There are several physical and chemical mechanisms that can be attributed to the improvement of the chemiresistor sensitivity and selectivity upon nanoparticles deposition. The improvement is determined by the two primary mechanisms associated with the surface doping of oxides with metal nanoparticles.

The first mechanism is determined by the differences in catalytic activity of nanoscale metals, which is known as the "spillover effect". The presence of nanoparticle dopants (e.g., $TiO_2$ nanoparticles) lowers the electronic work function and decreases the activation energy of the catalytic reaction occurring on the surface of the metal oxide nanograins. The products of catalysis occurring on the metal or metal oxide nanoparticles diffuse onto the metal oxide support (e.g., $SnO_2$), which acts as a reagent delivery system for the metal or metal oxide nanoparticle, amplifying the chemical processes occurring at the metal oxide surface (e.g., $SnO_2$), and dramatically modifying the oxide electronic behavior. The binding energy of the ionized oxygen species in the steady state, the catalytic reaction rate upon exposure to a vapor pulse, and the charge transfer rate from the surface to the bulk of the metal oxide (e.g., $SnO_2$) is strongly dependent on the electronic work function of the nanoparticles (e.g., $TiO_2$) and metal oxide support (e.g., $SnO_2$). Hence, the same analyte will generate different conductivity changes in chemiresistors functionalized with different nanoparticles (e.g., $TiO_2$ vs. Pt or $In_2O_3$ vs. $TiO_2$).

The functionalization of chemo resistor can be obtained by two different methods: surface modification, when deposition of metal oxide (e.g., SnO) is followed by deposition of modificator (e.g., $TiO_2$, Pt), or bulk modification when co-sputtering or multiple consecutive depositions of two metal oxides can be used in order to obtain nanocomposite material all through the volume of the sensor.

The second mechanism has a primarily physical nature, but also strongly depends on the work function of the vapor-sensitive materials. The deposition of nanoparticles (e.g., $TiO_2$, $In_2O_3$, Au, Pd, or Pt) on the surface of semiconductor layer (e.g., $SnO_2$ nanograins) or incorporating the nanoparticles (e.g., $TiO_2$, $In_2O_3$, Au, Pd, or Pt) all through the volume of the semiconductor layer (e.g., $SnO_2$ nanograins) leads to the formation of a large amount of nanoscale metal-semiconductor Schottky contacts (Schottky barriers) or semiconductor-semiconductor junctions (n-N or n-p junctions) over the metal oxide layer. The energy barrier height of the contacts is determined by the difference between the work functions W of the metal and semiconductor $\Delta E = Wm - Ws$ or difference in the work function between two different types of semiconductors $\Delta E = Ws1 - Ws2$. For example, the coating of SnO2 with catalytic nanoparticles such as Pt (W=5.12-5.93 eV), Pd (W=5.22-5.6 eV), Au (W=5.1-5.47 eV), Ni (W=5.04-5.35 eV), and Cu (W=4.53-5.1 eV) leads to a formation of Schottky contacts with different barrier heights. In the SnO2-nanoparticle chemiresistor, the external electrostatic potential is induced on nanoparticles by the adsorbed oxygen species. Exposure of the chemiresistor to a vapor pulse temporarily removes the adsorbed oxygen and causes a drop in the electrostatic potential induced on nanoparticle causing charge transfer from the nanoparticle to the semiconductor support. This mechanism of current modulation is similar to the field effect transistor, where the nanoparticle acts as a gate and the adsorbed oxygen molecules work as a source of electrostatic potential. Since the depletion depth and the amount of transferred charge are both determined by the value of $\Delta E$, the physical discrimination mechanism is also determined by the work functions of the nanoparticles and $SnO_2$ support.

In the present invention, the catalytic reaction activation energy is tuned in a desired manner. It now has been found that certain modifications make catalytic properties of sensors highly-preferential toward a particular analyte. In this way, the surface is able to trigger only the reactions with particular activation energy. The sensors of the present invention can be separated into five groups:
1. Sensors of gases acidic in nature: these sensors are $SnO_2$-based and tuned toward acidic sensitivity by surface doping with Cu nanoparticles forming basic oxide CuO. The basic nature of CuO makes the interactive layer very selective to acidic gases like $H_2S$ and mercaptans.
2. Sensors of gases basic in nature: these sensors are $SnO_2$-based and tuned toward basic sensitivity by surface doping with Mo nanoparticles forming acidic oxide $MoO_3$. These sensors have preferential sensitivity towards $NH_3$ and amines.
3. Sensors of oxidizing gases (e.g., $O_2$ and $NO_2$): these sensors are $SnO_2$-based and tuned toward oxidizing sensitivity by surface doping with Ni nanoparticles forming oxide NiO.
4. Sensors of reducing gases without well-pronounced acidic/basic properties (e.g., CO, $H_2$, and $CH_4$): these sensors are $SnO_2$-based and tuned toward reducing gases by surface doping with nanoparticles of noble metals forming quasi-stable clusters, e.g., $Pd_nO_m$ and $Pt_nO_m$.
5. Sensors of organic vapors (e.g., ethanol, benzene, toluene, ethylbenzene, xylene etc.): These sensors are $SnO_2$-based and tuned toward acidic sensitivity by doping with Fe nanoparticles forming basic oxide $Fe_2O_3$.

Deposition of Gas-Sensitive Layers:

In an aspect of the present invention the metal oxide and dopant layers are applied by sputtering. Conventional sensors are prepared by the standard sol-gel technique, which is based on deposition of small droplets of metal oxide paste. The present sputtering technique is superior to sol-gel method for the following reasons.

The first major drawback of sol-gel method is the large layer thickness, and hence limited sensitivity. Second, the deposition of microdroplets does not provide a complete control over the layer geometry and thickness. As a consequence of that, variations from sensor to sensor in this manufacturing process are unavoidable. Third, sensor response and recovery time for thick films is much longer than the thin films obtainable with sputtering, especially for large concentrations of analytes (gases). Because of the lack of control over sol-gel deposition, sensor voltage output cannot be predicted. Therefore, each sensor requires independent calibration using special gas mixes, which adds manufacturing cost and time. Oxide powder, used for paste preparation in sol-gel method, consists of micrograins, obtained by milling of bulk metal oxide. This technology is also known as top-down approach. Multiple studies indicate that microstructures obtained by top-down approach have relatively low chemical reactivity and sensitivity, compared to self-assembled nanograins, obtained by bottom-up approach (e.g., sputtering).

In contrast to the sol-gel method, the present sputtering method creates an ultra-thin layer of a precisely controlled geometrical shape. This provides: ultra-high sensitivity, ultra-fast response and recovery time, and elimination of variations from sensor to sensor. Sensor behavior becomes predicable, because the manufacturing process is fully controllable. Sensors formed this way can be implemented immediately and independent calibration of every device is no longer necessary for relatively high concentrations (50 ppm and higher). Of course, for ultra-precise sub-ppm measurements, calibration is still useful. Finally, the present manufacturing technique is based on self-assembly of metal-oxide structures of complex multi-oxide nature ($SnO_2/TiO_2$ or $SnO_2/In_2O_3$) and further possible surface functionalization with metal nanoparticles, also known as surface doping.

Integrated System Design, Manufacturing and Maintenance

The present manufacturing technique allows for fast manufacturing of large quantities of sensors (e.g., the simultaneous manufacturing of 624 chemical sensor platforms on a single wafer). For conventional sol-gel systems it would be equivalent to precise targeting and deposition of 2496 droplets, which is extremely expensive and time consuming.

Conventional integrated sensory systems are typically large in size. Discrimination power of an integrated sensor depends on the number of individual basic sensing elements with different catalytic properties. However, an increase in the number of sensors inevitably leads to an increase in size, which causes a non-uniform distribution of chemicals over the sensor array upon exposure to gaseous analyte leading to false recognition. In contrast to a conventional system, the disclosed highly-integrated system provides a physical placement of all the sensors at the same point (or nearly) in space. This design assures a uniform exposure of all the sensors to chemicals and, hence, an accurate recognition and concentration measurements.

Because of the large size, conventional integrated systems require sophisticated gas sampling systems, splitting the analyte gas into identical fractions for each sensor. Conventional integrated sensory systems typically have high manufacturing costs, especially in case of an advanced sampling system. Synchronization and calibration makes the manufacturing process time-consuming. Conventional integrated sensory systems typically have high power consumption (hundreds of watts). In contrast, the disclosed integrated system performs accurately even with a very primitive sampling system, can consume about tens of mV of power and has a manufacturing cost lower than that for a simple single-gas conventional sensor.

Operational Characteristics of Integrated Systems:

Individual sensors in the array evolve over time. This phenomenon is known as a long-term drift. For a conventional integrated system, individual elements evolve differently, causing failures of pattern recognition algorithms. Short-term drift due to the fluctuations in the environment also has different effect on individual elements and also causes instabilities in pattern recognition algorithms.

Frequently, individual sensors of a conventional integrated system have variances in time constant, response, and recovery time. This means that some of them respond to exposures faster than the others. Upon exposure to analyte, before reaching the stationary state, sensors of an integrated system go through a transient phase. If they are not well-synchronized, during the transient phase, the integrated system typically reports several false results. Synchronization of individual elements of a conventional integrated system is another time consuming process, and has to be implemented for each unit after the assembly.

An advantage of the present invention is that all the elements of the highly integrated array have the same dynamics for the long-term and short-term drift. Also, the time constant, response and recovery time is the same for all of them, meaning that the sensors are synchronized. Thanks to that the robust recognition is preserved even during the transient response.

In an aspect, the present invention provides a novel chemical sensor, comprising:
(a) an oxidized silicon wafer, comprising: a silicon layer sandwiched between a top ($1^{st}$) silicon oxide ($SiO_2$) layer and a bottom ($2^{nd}$) $SiO_2$ layer, the top $SiO_2$ layer, comprising: a sensor area;
(b) a heating element in contact with the $1^{st}$ $SiO_2$ layer and located near at least one edge of the sensor area;
(c) a pair of electrical leads in contact with the $1^{st}$ $SiO_2$ layer and at least partly located on the sensor area; and,
(d) a doped, metal oxide layer located on the sensor area and in contact with at least a part of the pair of electrical leads and the $1^{st}$ $SiO_2$ layer, wherein the doped, metal oxide layers, comprises:
(i) a $1^{st}$ metal oxide; and,
(ii) a $2^{nd}$ metal oxide.

In an aspect, the present invention provides a novel chemical sensor, comprising:
(a) an oxidized silicon membrane, comprising a silicon (Si) layer and a silicon oxide ($SiO_2$) layer, wherein the $SiO_2$ layer is located on top of the silicon layer and, comprises: a sensor area;
(b) a heating element in contact with the $SiO_2$ layer and located near at least one edge of the sensor area;
(c) a pair of electrical leads in contact with the $SiO_2$ layer and at least partly located on the sensor area; and,
(d) a doped, metal oxide layer located on the sensor area and in contact with at least a part of the pair of electrical leads and the $SiO_2$ layer, wherein the doped, metal oxide layers, comprises:
(i) a $1^{st}$ metal oxide; and,
(ii) a $2^{nd}$ metal oxide.

Membrane (sometimes referred to as a "floating" sensor) refers to a $SiO_2$/Si wafer that is typically formed from an oxidized silicon wafer (e.g., a wafer having $SiO_2$/Si/$SiO_2$ layers). The membrane is formed by removing one of the $SiO_2$ layers (e.g., the bottom layer) and a substantial portion of the Si layer. Typically part of the original wafer (e.g., $SiO_2$/Si/$SiO_2$) is left to serve as connectors for the membrane (e.g., leaving the 4 corner pieces of the original wafer as the "connectors" to the membrane).

In another aspect, the present invention provides a novel chemical sensor platform, comprising:
(a) an oxidized silicon wafer, comprising: a silicon layer sandwiched between a top ($1^{st}$) silicon oxide ($SiO_2$) layer and a bottom ($2^{nd}$) $SiO_2$ layer, the $1^{st}$ $SiO_2$ layer, comprising: a plurality of separate sensor areas;
(b) at least one heating element in contact with the $1^{st}$ $SiO_2$ layer and located near at least one edge of a sensor area;
(c) a plurality of electrical leads, each in contact with the $1^{st}$ $SiO_2$ layer, wherein 1 pair of electrical leads is at least partly located on each of the separate sensor areas;
(d) a plurality of doped, metal oxide layers, wherein 1 doped, metal oxide layer is located on each of the plurality of sensor areas and is in contact with at least a part of the pair of electrical leads located on the same area, wherein each doped, metal oxide layer, comprises:
i. a $1^{st}$ metal oxide; and,
ii. a $2^{nd}$ metal oxide.

In another aspect, the present invention provides a novel chemical sensor platform, comprising:
(a) an oxidized silicon membrane, comprising a silicon (Si) layer and a silicon oxide ($SiO_2$) layer, wherein the $SiO_2$ layer is located on top of the silicon layer and, comprises: a plurality of separate sensor areas;
(b) at least one heating element in contact with the $SiO_2$ layer and located near at least one edge of each sensor area;
(c) a plurality of pairs of electrical leads, each in contact with the $SiO_2$ layer, wherein 1 pair of electrical leads is at least partly located on each of the separate sensor areas;
(d) a plurality of doped, metal oxide layers, wherein 1 doped, metal oxide layer is located on each of the plurality of sensor areas and is in contact with at least a part of the pair of electrical leads located on the same area, wherein each doped, metal oxide layer, comprises:
i. a $1^{st}$ metal oxide; and,
ii. a $2^{nd}$ metal oxide.

The number of sensor areas in the chemical sensor platform varies. Examples include 2, 3, 4, 5, 6, 7, 8, 9, 10, or more. The number of sensor areas determines the number of pairs of electrical leads, and doped, metal oxide layers. The number of heating elements is independent of the number of sensor areas. One heating element can service more than one sensor area. Examples of the number of heating elements includes 1, 2, 3, 4, 5, or more.

In another aspect, the plurality is 4. In another aspect, the number of sensor areas is 4.

In another aspect, in the chemical sensor platform there are 4 separate sensor areas, 1 heating element, 4 pairs of electrical leads, and 4 doped, metal oxide layers.

In another aspect, in the chemical sensor platform there are 4 separate sensor areas, 1 Pt heating element, 4 pairs of Pt electrical leads, and 4 $SnO_2$/$TiO_2$ metal oxide layers.

In another aspect, in the chemical sensor platform there are 4 separate sensor areas, 1 Pt heating element, 4 pairs of Pt electrical leads, 4 $SnO_2$/$TiO_2$ metal oxide layers, and 4 Si/$SiO_2$ connectors.

In another aspect, in the chemical sensor platform there are 4 separate sensor areas, 1 Pt heating element, 4 pairs of Pt electrical leads, 4 $SnO_2/TiO_2$ metal oxide layers, and 4 $SiO_2/Si/SiO_2$ connectors.

In another aspect, in the chemical sensor platform there are 4 separate sensor areas, 1 Pt/Ti (Ti being the 2nd material) heating element, 4 pairs of Pt/Ti (Ti being the 2nd material) electrical leads, and 4 4 $SnO_2/TiO_2$ metal oxide layers.

In another aspect, in the chemical sensor platform there are 4 separate sensor areas, 1 Pt/Ti (Ti being the 2nd material) heating element, 4 pairs of Pt/Ti (Ti being the 2nd material) electrical leads, 4 $SnO_2/TiO_2$ metal oxide layers, and 4 $Si/SiO_2$ connectors.

In another aspect, in the chemical sensor platform there are 4 separate sensor areas, 1 Pt/Ti (Ti being the 2nd material) heating element, 4 pairs of Pt/Ti (Ti being the 2nd material) electrical leads, 4 $SnO_2/TiO_2$ metal oxide layers, and 4 $SiO_2/Si/SiO_2$ connectors.

The description herein applies to both sensors and platforms, where ever appropriate.

In another aspect, wherein the $1^{st}$ and $2^{nd}$ metal oxides of the doped, metal oxide layer, are simultaneously deposited via sputtering.

In another aspect, each $1^{st}$ metal oxide is independently selected from: $SnO_2$, $ZnO$, $V_2O_5$, $WO_3$, $TiO_2$, $Al_2O_3$, and $Fe_2O_3$. In another aspect, each $1^{st}$ metal oxide is $SnO_2$.

In another aspect, each $2^{nd}$ metal oxide is independently selected from: $TiO_2$, Au, CuO, $Cu_2O$, $MoO_2$, $MoO_3$, NiO, $Ni_2O_3$, Pt, Pd, AgO, $RuO_2$, $Rh_2O_3$, $OsO_2$, $OsO_4$, $IrO_2$, and $In_2O_3$. In another aspect, each $2^{nd}$ metal oxide is $In_2O_3$. In another aspect, each $2^{nd}$ metal oxide is $TiO_2$.

In another aspect, each doped, metal oxide layer is independently about 5, 10, 15, 20, 25, 30, 35, to 40 nm thick.

In another aspect, for each doped, metal oxide layer, the weight % of the $1^{st}$ metal oxide is from 50-99% and the weight % of the $2^{nd}$ metal oxide (dopant) is from 1-50%. The weight % is based on energy dispersive analysis X-Ray (EDAX) of the sensing layer. Examples of the weight % of the $1^{st}$ metal oxide include: 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 69, 97, 98, and 99. Examples of the weight % of the $2^{nd}$ metal oxide include: 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, and 1.

In the chemical sensor (or platform), the $1^{st}$ $SiO_2$ layer is typically polished. The sensor area is where at least part of a pair of electrical leads is located as well as the metal oxide and dopant layers. The heating element is not in contact with the electrical leads, the metal oxide layer, or the dopant layer but is located close enough to be able to heat the metal oxide and dopant layers. The dopant layer substantially if not entirely covers the exposed or top side of the metal oxide layer.

In another aspect, the oxidized silicon wafer is about 100, 150, 200, 250, 300, 350, 400, 450, to 500 μm thick. In another aspect, the oxidized silicon wafer is about 200 μm thick.

In another aspect, the part of the 2nd $SiO_2$ layer located beneath the plurality of sensor areas (or sensor area, if only 1 is present) is absent and a substantial portion of the corresponding silicon layer is absent. In this aspect, part of the bottom of the wafer is absent, including all of the 2nd $SiO_2$ layer and some of the bottom of the silicon layer.

In another aspect, the corresponding part of the silicon layer located beneath the plurality of sensor areas (or sensor area, if only 1 is present) is about 5, 10, 15, 20, 25, 30, 35, 40, 45, 50, 55, 60, 65, 70, 75, 80, 85, 90, 95, to 100 μm thick. This is measured from the bottom of the $1^{st}$ $SiO_2$ layer to the bottom of the wafer (no $2^{nd}$ $SiO_2$ layer is present on this part of the silicon layer). In another aspect, the corresponding part of the silicon layer located beneath plurality of sensor areas (or sensor area, if only 1 is present) is about 50 μm thick.

In another aspect, part of the $1^{st}$ $SiO_2$ layer at the edges of the plurality of sensor areas (or sensor area, if only 1 is present) is absent, thereby forming a discontinuous trench around the plurality of sensor areas (or sensor area, if only 1 is present). The $1^{st}$ $SiO_2$ layer that is in contact with the electrical leads remains. The absence of the $1^{st}$ $SiO_2$ layer at the edges of the sensor area, but not including the $1^{st}$ $SiO_2$ layer that is in contact with the electrical leads, creates a trench that partially isolates the $1^{st}$ $SiO_2$ layer in the sensor area from the $1^{st}$ $SiO_2$ layer outside of the sensor area. This trench can be deepened by removal of the silicon at the bottom of the trench. Finally, when the $2^{nd}$ $SiO_2$ under the sensor area is removed and part of the corresponding part of the silicon layer is removed, the trench becomes an actual opening. The remaining $1^{st}$ $SiO_2$ layer in the sensor area and the corresponding silicon layer underneath are then "floating". The floating area is called a membrane.

In another aspect, part of the $1^{st}$ $SiO_2$ layer at the edges of the plurality of sensor areas (or sensor area, if only 1 is present) and part of the corresponding silicon layer is absent, thereby forming a discontinuous trench around the plurality of sensor areas (or sensor area, if only 1 is present).

In another aspect, in the chemical platform (or chemical sensor):

i. the part of the $2^{nd}$ $SiO_2$ layer located beneath the plurality of sensor areas (or sensor area, if only 1 is present) is absent and a substantial portion of the corresponding part of silicon layer is absent; and, ii. the part of the $1^{st}$ $SiO_2$ layer at the edges of the plurality of sensor areas (or sensor area, if only 1 is present) and the silicon layer directly beneath is absent, thereby forming a discontinuous opening around the plurality of sensor areas (or sensor area, if only 1 is present).

In another aspect, the corresponding part of the silicon layer is about 5, 10, 15, 20, 25, 30, 35, 40, 45, 50, 55, 60, 65, 70, 75, 80, 85, 90, 95, to 100 μm thick. This is measured from the bottom of the 1st $SiO_2$ layer to the bottom of the wafer (no 2nd $SiO_2$ layer is present on this part of the silicon layer). In another example, the corresponding part of the silicon layer is about 50 μm thick.

In another aspect, the $1^{st}$ and $2^{nd}$ $SiO_2$ layers (in the sensor or platform) are independently about 200, 250, 300, 350, to 400 nm thick. In another aspect, the $1^{st}$ and $2^{nd}$ $SiO_2$ layers are independently about 300 nm thick.

In another aspect, the $1^{st}$ metal oxide of the plurality of doped, metal oxide layers is the same. In another aspect, the $1^{st}$ metal oxide of the plurality of doped, metal oxide layers is different. In another aspect, all of the $1^{st}$ metal oxide layers are the same thickness. In another aspect, all of the $1^{st}$ metal oxide layers are of different thicknesses.

In another aspect, the $2^{nd}$ metal oxide of the plurality of doped, metal oxide layers is the same. In another aspect, the $2^{nd}$ metal oxide of the plurality of doped, metal oxide layers is different. In another aspect, all of the $2^{nd}$ metal oxide layers are the same thickness. In another aspect, all of the $2^{nd}$ metal oxide layers are of different thicknesses.

In another aspect, the at least one heating element (or heating element for the chemical sensor), independently comprises: a $1^{st}$ material selected from Pt, Au, and polysilicon. In another aspect, the at least one heating element, comprises: Pt.

In another aspect, the heating element is about 50, 100, 150, 200, 250, 300, 350, 400, 450, 500, 550, 600, 650, 700, 750, 800, 850, 900, 950 to 1,000 nm thick. In another aspect, the heating element is about 300 nm thick.

In another aspect, the heating element, further comprises: a $2^{nd}$ material layer sandwiched between the $1^{st}$ $SiO_2$ layer and the $1^{st}$ material layer. In another aspect, the $2^{nd}$ material layer, comprises: a metal selected from Ti and Cr. In another aspect, the $2^{nd}$ material layer, comprises: Ti. In another aspect, the $2^{nd}$ material layer is about 1, 2, 3, 4, 5, 6, 7, 8, 9, to 10 nm thick. In another aspect, the $2^{nd}$ material layer is about 2 nm thick. In another aspect, the $2^{nd}$ material layer is about 5 nm thick.

In another aspect, the plurality of electrical leads (or electrical lead in the chemical sensor), comprise: a $1^{st}$ metal layer independently selected from Pt and Au. In another aspect, the plurality of electrical leads, comprise: Pt. In another aspect, the plurality of electrical leads are about 50, 100, 150, 200, 250, 300, 350, 400, 450, 500, 550, 600, 650, 700, 750, 800, 850, 900, 950 to 1,000 nm thick. In another aspect, the plurality of electrical leads (or lead in the chemical sensor) are about 300 nm thick.

In another aspect, the plurality of electrical leads (or electrical lead in the chemical sensor), each further comprise: a $2^{nd}$ metal, layer sandwiched between the $1^{st}$ $SiO_2$ layer and the $1^{st}$ metal layer. In another aspect, each $2^{nd}$ metal layer, comprises: a metal independently selected from Ti and Cr. In another aspect, each $2^{nd}$ metal layer, comprises: Ti. In another aspect, each $2^{nd}$ metal layer is independently about 1, 2, 3, 4, 5, 6, 7, 8, 9, to 10 nm thick. In another aspect, each $2^{nd}$ metal layer is independently about 2 nm thick. In another aspect, each $2^{nd}$ metal layer is independently about 5 nm thick.

In another aspect, the $2^{nd}$ $SiO_2$ layer under the sensor area is absent and the thickness of the sensor area, as measured from the top of the dopant layer to the bottom of the silicon layer (i.e., the thickness of the sensor membrane), is from 50, 100, 150, 200, 250, 300, 350, 400, 450 to 500 µm. In another aspect, the membrane thickness is 200 µm. In another aspect, the membrane thickness is 100 µm.

In another aspect, the part of the $2^{nd}$ $SiO_2$ layer located beneath the plurality of sensor areas is absent and a substantial portion of the corresponding silicon layer is absent.

In another aspect, the portions (or portion for the chemical sensor) of the $2^{nd}$ $SiO_2$ layer under the corresponding plurality of sensor areas (or area for the chemical sensor) is absent and the thickness of the plurality of sensor areas (or area), as measured from the top of the corresponding dopant layers to the bottom of the corresponding silicon layers (or layer)(i.e., the thickness of the plurality of sensor membranes (or sensor membrane)), is from 50, 100, 150, 200, 250, 300, 350, 400, 450 to 500 µm. In another aspect, the thickness of the plurality of membranes (or membrane) is 200 µm. In another aspect, the thickness of the plurality of membranes (or membrane) is 100 µm. In another aspect, the thickness of the plurality of membranes (or membrane) is 50 µm.

In another aspect, the present invention provides a novel method of forming a chemical sensor platform, comprising:
(a) depositing at least one heating element and a plurality of pairs of electrical leads (e.g., 4 pairs) onto an oxidized silicon wafer, wherein:
  i. the oxidized silicon wafer, comprises: a silicon layer sandwiched between a top ($1^{st}$) silicon oxide ($SiO_2$) layer and a bottom ($2^{nd}$) $SiO_2$ layer;
  ii. the $1^{st}$ $SiO_2$ layer, comprises: a plurality of separate sensor areas (e.g., 4);
  iii. the at least one heating element and plurality of pairs of electrical leads are deposited onto the $1^{st}$ $SiO_2$ layer;
  iv. the at least one heating element is located near at least one edge of at least one sensor area; and,
  v. 1 pair of electrical leads is at least partly located on each of the separate sensor areas (e.g., 4 pairs);
(b) depositing a doped, metal oxide layer onto each of the plurality of sensor areas and the 1 pair of electrical leads located thereon, wherein the doped, metal oxide layer, comprises:
  i. a $1^{st}$ metal oxide; and,
  ii. a $2^{nd}$ metal oxide; and,
(c) annealing the resulting platform at a sufficient temperature and for a sufficient time to cause at least a portion of each $1^{st}$ metal oxide (e.g., 4 $1^{st}$ metal oxides) to form nanograins and at least a portion of each $2^{nd}$ metal oxide (e.g., 4 $2^{nd}$ metal oxide) to form nanoparticles.

Nanocrystals are the building blocks of nanograins/nanoparticles. Nanocrystals agglomerate into nanograins/nanoparticles (nanograins being larger than nanoparticles). The size of nanograins/nanoparticles vary in a range from about 5, 10, 15, 20, 25, 30, 35, 40, 45, 50, 55, 60, 65, 70, 75, 80, 85, 90, 95, to 100 nm, depending on the type of material and its ability to agglomerate into bigger particles.

In another aspect, the $1^{st}$ and $2^{nd}$ metal oxides of the doped, metal oxide layer, are simultaneously deposited via sputtering.

In the method, each metal oxide layer is in contact with at least a part of 1 pair of electrical leads and part of the sensor area not covered by the electrical leads. It is noted that neither the electrical leads nor the metal oxide layer is typically in contact with the heater. The dopant layer is substantially the same dimensions as the metal oxide layer and substantially covers the top side of the metal oxide layer.

In another aspect, the method, further comprises:
(d) etching away part of the $1^{st}$ $SiO_2$ layer at the edges of the plurality of sensor areas and part of the corresponding silicon layer to form a discontinuous trench around the plurality of sensor areas.

In another aspect, the method, further comprises:
(e) etching away the part of the $2^{nd}$ $SiO_2$ layer located beneath the plurality of sensor areas and part of the corresponding silicon layer, wherein enough of the silicon layer is removed to convert the discontinuous trench into a discontinuous opening in the silicon wafer.

In another aspect, plurality is 4.

In another aspect, etching (f) is completed prior to annealing (e).

In another aspect, the method, further comprises:
(f) prior to depositing (a), applying a $1^{st}$ photomask to the $1^{st}$ $SiO_2$ layer; and,
(g) after depositing (a), removing the $1^{st}$ photomask.

In another aspect, the method, further comprises:
(h) prior to etching (e), applying a $2^{nd}$ photomask to the $1^{st}$ $SiO_2$ layer; and,
(i) after etching (e), removing the $2^{nd}$ photomask.

In another aspect, the method, further comprises:
(j) prior to depositing (b), applying a 3$^{rd}$ photomask to the 1$^{st}$ SiO$_2$ layer; and,
(k) after depositing (c), removing the 3$^{rd}$ photomask.

In another aspect, the method, further comprises:
(l) prior to etching (f), applying a 4$^{th}$ photomask to the 2$^{nd}$ SiO$_2$ layer; and,
(m) after etching (f), removing the 4$^{th}$ photomask.

In another aspect, the method, further comprises:
(n) prior to depositing (a), depositing an adhesive metal layer The adhesive metal layer is the 2$^{nd}$ material layer sandwiched between the 1$^{st}$ SiO$_2$ layer and the 1$^{st}$ material layer.

In another aspect, the present invention provides a novel, integrated chemical sensor that can be used in the following applications:
a. Sensor components for confined space gas monitors, leak detectors and analytical instruments. The present sensor can replace traditional metal oxide sensors in their standard applications for gas detection. The application determines the type of sampling system (active or passive).
b. Analytical instruments for analysis of chemical compounds in natural gas and oil
c. Detectors of explosives
d. Breathalyser for analysis of THC and other drugs and their metabolites in the human breath.
e. Alcohol monitors inside vehicles for prevention of drunk driving.
f. Sensors utilized in cooking processes for prevention of overcooking and burning.
g. Built-in sensors for cell phones
h. Built-in sensors for microphones.
i. Built-in sensors for food freshness and safety monitoring for refrigerators.

EXAMPLES

The following examples are meant to illustrate, not limit, the present invention.

Example 1

A general description of the novel manufacturing process for making sensors and the highly-integrated sensors of the present invention is as follows:

Starting Substrate:

An oxidized silicon wafer is used as the substrate for the sensors and platforms of the present invention. A platform of the present invention is a unit that comprises multiple sensors and pairs of electrical leads and at least one heating element. The present manufacturing process allows for numerous platforms to be formed simultaneously on one oxidized silicon wafer. As will be described below, each platform may contain only one type of sensor (e.g., all sensors have the same doped, metal oxide layers) or each sensor on the platform may have a variety of different sensor types (e.g., 2, 3, 4, or more).

A typical wafer is 4" in diameter, but a larger wafer (e.g., 6" in diameter) can be used in order to increase the number of devices per manufacturing cycle and decrease the manufacturing cost per device. The orientation of the wafer can be 100. One side (the "top" side) of the wafer is typically polished. An example of the thickness of the wafer is 200 µm. Other examples of the thickness of the wafer include from about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to 500 µm thick. The thinner the wafer (e.g., 200 µm, 150 µm, or 100 µm), the lower the power consumption of the resulting device.

A 1$^{st}$ layer of oxidized silicon (SiO$_2$) is present on the top of the wafer. A 2$^{nd}$ layer of oxidized silicon (SiO$_2$) is present on the bottom of the wafer. Since the wafer is polished, it is the 1$^{st}$ layer of SiO$_2$ that is polished. An example of the thickness of the oxide layers is about 300 nm. Other examples of the thickness of the SiO$_2$ layers include from about 200, 210, 220, 230, 240, 250, 260, 270, 280, 290, 300, 310, 320, 330, 340, 350, 360, 370, 380, 390 to 400 nm thick.

Applying Photomask #1

Each sensor has to be thermally activated in order to act as a conductometric sensor. Thus, a microheater (heating element) has to be deposited for each sensor or on each platform. Also, interdigitated metal terminals (electrical leads) have to be deposited for monitoring of signals from each of the sensor areas (change in conductance caused by a chemical reaction). Patterns for both the microheater and terminals, for the numerous platforms that can be simultaneously made, can be deposited on the wafer using photolithography, as follows.

A photoresist (Photomask #1) is spin coated on the front side (i.e., polished side) of the wafer. The photoresist is chosen based on its desired thickness (thick enough to allow for deposition of the heater and metal leads, but not too thick to make it difficult to use). For example, photoresist 1827, a positive photoresist that is expected to produce a 2.7 µm layer @ 4000 rpm spin, can be used. It is applied by spinning the wafer for 0.2 sec@ 500 rpm while the photoresist is applied, and then for 10 sec @ 4000 rpm. Other examples of the thickness of the photoresist to be applied include from about 2, 3, 4, 5, 6, 7, 8, 9, to 10 µm.

After spin coating, the wafer is "soft baked" by heating at (e.g., 90° C. in air for about 70-75 sec). The "soft baked" wafer is then exposed to UV light appropriate for the photoresist (e.g., 325 W for about 22 seconds), followed by a toluene bath (60 sec), blow drying with N$_2$, and another soft baking (e.g., 90° C. in air for about 15 sec).

In order to remove the unwanted portions of the photoresist, it must be developed, rinsed, and dried. For example, the photoresist can be developed by contacting with a developing agent (e.g., MF-24A for 90 sec), followed by a Quick Dump Rinse (QDR) with dionized water. Finally, the rinsed wafer can then dried via a Spin Rinse Dryer (SRD). For example, it can be spun for 30 sec @ 500 rpm with a deionized water spray, then 3 min @ 2000 rpm under a N$_2$ gas flow, and finally for 3 min @ 4000 rpm in air to dry.

The quality of photolithography can be verified by optical microscopy to match the desirable percent of defects, desired geometry, and the photoresist free area. If the photoresist is not fully removed, the wafer can be placed in the developer bath (e.g., contacted with MF-24A) for an additional 10-15 sec, then cleaned via the QDR and SRD methods and then checked again by optical microscopy.

Heater and Electrical Lead Deposition

With the photomask applied, the heater and electrical leads are then formed. One way to achieve thin and uniform layers of heater and/or electrical leads (as well as the other layers/components of the sensor) is via sputtering. Other techniques including atomic layer deposition, chemical vapor deposition, and thermal evaporation can also be used for the heater and electrical leads, as well as for the other layers/components of the sensor.

Optionally an adhesive layer (e.g., Ti or Cr) can be deposited first, followed by the desired material for heater (e.g., Pt, Au, or poly-silicon) and/or electrical lead (Pt and Au). The adhesive layer can be deposited by sputtering using an appropriate target (e.g., a Ti wafer).

An example of the thickness of the optional adhesive layer is about 2 nm. Another example is about 5 nm. Other examples of the thickness of the optional adhesive layer include from about 1, 2, 3, 4, to 5 nm. An example of the thickness of the electrical lead is about 300 nm. Other examples of the thickness of the electrical lead include from about 100, 150, 200, 250, 300, 350, 400, 450, 500, 550, 600, 650, 700, 750, 800, 850, 900, 950, to 1000 nm. An example of the thickness of the heater is about 300 nm. Other examples of the thickness of the heater include from about 100, 150, 200, 250, 300, 350, 400, 450, 500, 550, 600, 650, 700, 750, 800, 850, 900, 950, to 1000 nm.

It can also be desirable to deposit alignment marks to allow for additional photomasks to be aligned. These marks are not limited by shape (e.g., X's, crosses, boxes, etc.) and need only be large enough to be seen when aligning another photomask.

Removing Photomask #1:

Once the electrical leads and heater have been applied, Photomask #1 is removed to allow for the deposition of the metal oxide layer. Photomask #1 can be removed using standard technology. For example, the modified wafer can be placed in an acetone bath for 2 hours at 60-70° C. The wafer can then be placed in a sonicated bath for 5-10 min to remove the remaining metal coated photoresist. An optical microscope can be used for quality control of metal deposition. The thickness of the deposited metal layer can then be verified using a contact profilometer.

FIG. 1 shows an example of a part of a wafer (green) to which a heating element (white area surrounding the green "T" in the middle) and electrical leads (interdigitated terminals)(remaining white area) have been deposited and Photomask #1 has been removed. The heater in this figure separates 4 sensor areas.

In another aspect, the heater and electrical leads are different materials, e.g., a poly-silicon heater and Pt leads. If different materials are chosen, then an additional photo-masking step will be necessary. Either the heater or electrical leads are applied while the location on the wafer for the other is protected. Photomask #1 is then removed and #1A is applied to allow for the other of the heater or electrical leads to be applied. Photomask #1A is then removed. The structure shown in FIG. 1 could also be an example wherein the heater and electrical leads are different materials.

Applying Photomask #2:

In order to deposit the metal oxide, the heater (and optionally other parts of the wafer) needs to be protected. Photomask #2 can be applied similarly to the Photomask #1. It is useful to be able to align Photomask #2 with Photomask #1. For example, Photomask #1 can have crosses on both sides of the mask and Photomask #2 can have squares.

As with Photomask #1, the quality of photolithography should be verified by optical microscopy to match the geometry and desirable percent of defects. If the developed photoresist is not fully removed, the wafer should be placed again in the developer (e.g., contacted with MF-24A for an additional 10-15 sec), then cleaned via the described QDR and SRD methods and checked again by optical microscopy.

Figure 2:
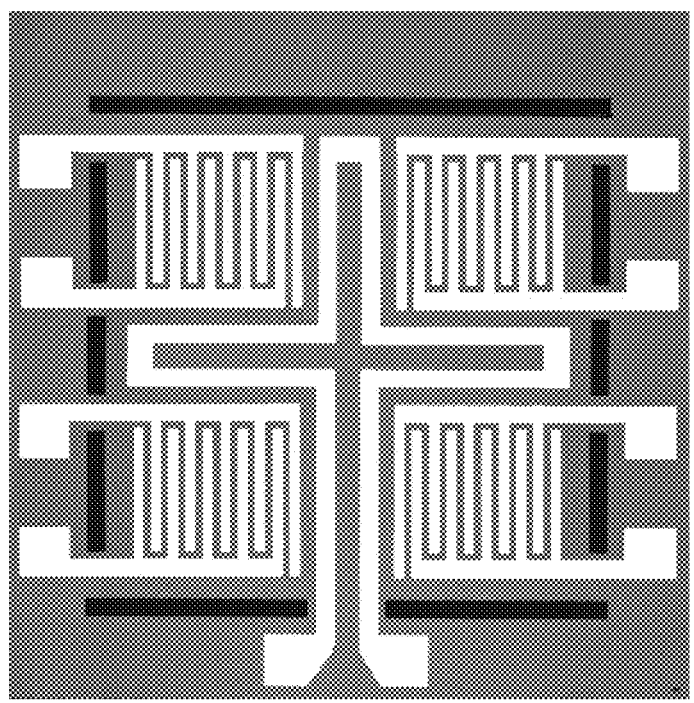
FIG. 2 shows a wafer (green) after trenching (black areas, etched silicon) and removal of the photomask. The wafer is 1.875×1.875 mm.

Trenching:

RIE etching: One way to decrease the power required to heat the metal oxide is to substantially isolate the sensor area from the surrounding wafer. This can be achieved first by RIE etching of the $SiO_2$ layer to form a discontinuous trench around the sensor area (see the black lines shown in FIG. 2).

The trench is discontinuous as the $SiO_2$ under the electrical leads and heater is not removed. The etched area can be inspected under an optical microscope. The process is repeated if necessary to remove the $SiO_2$ completely in the desired areas.

One way to separate the platforms from the wafer is via etching. For example, the $SiO_2$ from an outline around each platform can be etched as a part of the RIE etching process. This begins the process of creating 624 separate sensor platforms from the original wafer.

Before proceeding to etch part of the silicon layer, it is useful to measure the thickness of the photoresist. If the photoresist thickness is less than 2~µm after RIE, then the photo resist can be removed and reapplied. A thicker photoresist (e.g., SPR 220-7 (provides ~7 µm layer at 4000 rpm)) can be chosen to protect the features from the DRIE etching that is to follow. It can be beneficial to trench with DRIE immediately after removing the $SiO_2$ layer to avoid new oxide formation.

DRIE etching: Prior to DRIE etching, the silicon wafer is protected by attaching a support silicon wafer (e.g., a 500 µm support silicon wafer) to the back side of the silicon wafer. The support wafer protects the processed wafer from being broken in the DRIE chamber. The silicon on the front side of the wafer that was exposed during RIE etching is then etched via DRIE. The etched area is inspected under optical microscope. The process is repeated if necessary to finish removing the unwanted silicon.

If the platforms are to be separated by etching, this process can be continued with the DRIE. For example, the silicon in the outline around each platform formed by the above $SiO_2$ etching can also be etched to continue the process of creating 624 separate sensor platforms from the original wafer.

Removing Photomask #2:

Photomask #2 can then be removed using the lift-off process described for Photomask #1.

Sensing Element Fabrication:

A third photomask (Photomask #3) can be applied similarly to the Photomask #1 and aligned similarly to Photomask #2 (e.g., squares on Photomask #3 can be aligned with crosses from Photomask #1). As with Photomask #1, the quality of photolithography should be verified by optical microscopy to match the geometry and desirable percent of defects. If the developed photoresist is not fully removed, the wafer should be placed again in developer (e.g., contacted with MF-24A for an additional 10-15 sec), then cleaned via the described QDR and SRD methods and checked again by optical microscopy.

With Photomask #3 in place, a doped metal oxide can be deposited. A useful method of depositing the doped, metal oxide layer is via co-sputtering (both metal oxide and dopant are sputtered simultaneously). This method allows one to precisely control the thickness of the layer being deposited and also provides a consistent and repeatable process for forming the metal oxide layer (as opposed to methods such as using a sol-gel paste). The nanograins/nanoparticles are formed during the annealing process (see below).

One example of a $1^{st}$ metal oxide is $SnO_2$. Other examples include ZnO, $V_2O_5$, $WO_3$, $TiO_2$. $Al_2O_3$, $In_2O_3$ and $Fe_2O_3$.

One example of a $2^{nd}$ metal oxide (dopant) is $TiO_2$ (the $TiO_2$ can be sputtered as $TiO_2$ or as Ti and then oxidized via annealing). Other examples include $TiO_2$, Au, CuO, $Cu_2O$, $MoO_2$, $MoO_3$, NiO, $Ni_2O_3$, Pt, Pd, AgO, $RuO_2$, $Rh_2O_3$, $OsO_2$, $OsO_4$, $IrO_2$, and $In_2O_3$. The dopant if sputtered as a non-oxide metal (e.g., Ti, Au, Cu, Mo, Ni, Pt, Pd, Ag, Ru, Rh, Os, Ir, and In) is typically, with the exception of Au, Pt, and Pd, oxidized during annealing (see below). This oxidation process oxidizes part of the dopant (typically the area exposed to oxygen), but does not necessarily oxidize all of the dopant. For example, some of the dopant inside may still be in an unoxidized state. Au, Pt, and Pd, while not forming oxides during annealing, do form quasi-oxide states on their surfaces (e.g., quasi-stable clusters such as $Pd_nO_m$ and $Pt_nO_m$).

An example of the thickness of the doped, metal oxide layer is about 36 nm. Other examples of the thickness of the doped, metal oxide layer include from about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to 50 nm depending on desired the oxide parameters. The thickness of the doped, metal oxide layer can be measured by a contact profilometer.

The different combinations of metal oxide and dopant provide different sensitivities to different gases.

With the metal oxide layer formed, Photomask #3 can be removed as described for Photomask #1.

Different Sensing Elements:

If the sensor platform contains sensors with different doped metal oxides and/or (i.e., different sensors), then the process of applying a photomask, developing it, forming the doped, metal oxide layers, and removing the photomask is repeated for as many times as necessary. For example, if each platform contains 4 different sensors separated by a heater (similar to the structure shown in FIG. 2), then process of applying the doped, metal oxide layers will be repeated three addition times (Photomasks 3A, 3B, and 3C will be used) to provide a sensor with 4 distinct doped, metal-oxide sensing areas.

"Floating" Sensor Formation:

After all the sensing elements are deposited and doped, the bottom of the wafer is then etched to remove the $SiO_2$ layer under the sensor area (where the doped, metal oxide layers are located) as well as a substantial part of the bottom of the silicon layer. For example, if the silicon layer is 200 µm thick, then about 150 µm can be removed, thereby leaving only about 50 µm of silicon under the sensor and creating a "floating" sensor by removing enough silicon to convert the trenches previously formed into openings (i.e. holes). Removal of the silicon and forming the openings reduces the energy needed to power the sensor platform (and resulting integrated sensor).

The features on the top of the wafer should be protected with a layer of photoresist (e.g., photoresist 1813 can be applied). The bottom of the wafer can now be modified.

A photoresist (Photomask #4)(e.g., photoresist SPR 220-7) can be applied onto the backside (unmodified side) of the wafer similarly to previous photomasks. After exposure to UV light and developed, the photomask is complete and etching can begin. Photomask #4 is typically thicker than Photomasks #1-3 because of the amount of silicon being removed during the DRIE process. As a result, more time is usually required to allow the thicker photoresist layer, e.g., 4-10 µm to cure.

The bottom $SiO_2$ layer can be removed via RIE. The etched area is then inspected under optical microscope. The process is repeated if necessary to remove the oxide completely.

If the platforms are to be separated by etching, this process can be continued with the RIE on the bottom of the wafer. For example, the $SiO_2$ on the bottom of the wafer that is under the outline formed above around each platform can also be etched to continue the process of creating 624 separate sensor platforms from the original wafer.

Next part of the silicon layer is removed via DRIE. It can be beneficial to start DRIE right after removing the oxide to avoid new oxide formation over time.

Due to the harsh conditions of the DRIE process, the silicon wafer can first be protected by attaching a support silicon wafer (e.g., a 500 µm support silicon wafer) to the top side of the silicon wafer. The support wafer protects the processed wafer from being broken in the DRIE chamber. Once the top of the silicon has been protected, silicon from the bottom can then be etched, e.g., ~150 µm, via DRIE. The etched area is inspected under optical microscope. The process is repeated if necessary to complete removal of the desired amount of silicon.

If the platforms are to be separated by etching, this process can be completed with the DRIE on the bottom of the wafer. For example, the silicon in the outline around each platform formed by $SiO_2$ etching on the bottom can also be etched to complete the process of cutting all the way through the wafer and of creating 624 separate sensor platforms from the original wafer.

With the removal of $SiO_2$ and silicon complete, Photomask #4 can be removed as described for Photomask #1.

The amount of silicon removed from under the sensing area depends on the desired thickness of the "floating" sensor. One example of the thickness of silicon under the sensing area is 50 µm. Other examples include from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, to 60 µm.

Figure 3:
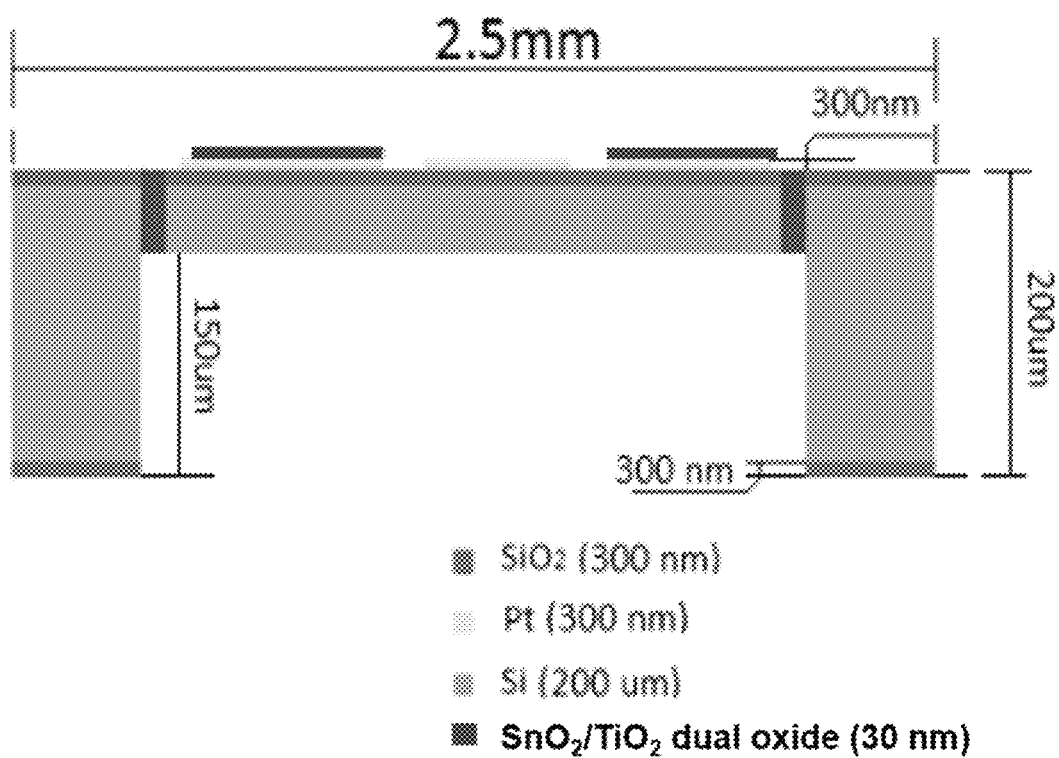
FIG. 3 shows an example of a "floating sensor" (which can also be referred to as a membrane with $SiO_2/Si/SiO_2$ connectors).

An example of the "floating" sensor of the present invention is shown in FIG. 3. The dark grey lines on either side of the Pt leads represents discontinuous openings (holes) in the wafer that were created by the RIE/DRIE trenching and then RIE/DRIE removal of the bottom side of the wafer.

The depth of the DRIE is typically such that it cuts apart the platforms without the need for mechanical cutting. Optionally, one can reduce the depth of the DRIE etching and then cut the platforms apart mechanically.

Sensor Packaging

Bonding conditions: Gold wire diameter 25 µm, substrate temperature 130° C., tail 2, loop 2. Kulicke & Soffa Wire bonder Model 4500.

a. First bond (ball bond): force 2, power 2, time 2.
b. Second bond (wedge bond): force 3, power 2.5, time 2.

With the sensor platform complete, it is then connected to a package in order to be incorporated into an integrated chemical sensor. The surface of each sensor's platform has to be leveled with the package pin holders in order to improve the bonding contacts and prevent the wire from breaking or being stuck inside the soldering capillary. The sensors cup are attached in order to complete the integrated sensor package.

Sensor Annealing

In order for nanoparticles and nanograins to form in the doped, metal oxide layers, and if necessary to oxidize the $2^{nd}$ metal oxide (if deposited as non-oxide, e.g., Ti or In), the sensor is annealed in the presence of oxygen (e.g., air or synthetic air). The annealing can be conducted prior to packaging. However, a benefit of annealing after packaging is that the platform need not be touched post packaging.

Annealing temperature: 200-900° C., including 200, 250, 300, 350, 400, 450, 500, 550, 600, 650, 700, 750, 800, 850, to 900° C.

Annealing time: 1-40 hours, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, to 40 hours.

Annealing atmosphere: an oxygen-containing gas, including air and synthetic air.

The temperature chosen is dependent up on the components of the sensor and its desired use. The size of the grains/particles and their morphology can be observed via SEM (scanning electron microscope), AFM (atomic force microscope), and/or XRD (x-ray diffraction).

During the annealing process metal oxide grains (nanograins) of the $1^{st}$ metal oxide are formed from the amorphous, sputtered structure. The size of the grains (e.g., 5-20 nm) impacts the sensitivity of the sensor.

During the annealing process the dopant ($2^{nd}$ metal oxide), if not already oxidized (e.g., Ti sputtered as opposed to $TiO_2$), oxides and dopant nanoparticles are formed. The formation of dopant nanoparticles causes the continuous amorphous layer (e.g., formed via sputtering) is crystallized to form a polycrystalline structure.

In one example, the annealing temperature for $SnO_2$ is 700° C., for 4 hours.

In one example, the annealing temperature for ZnO is 700° C., for 4 hours.

Example 2

Examples of the weight percentages of doped, metal oxide layers of the present invention are shown in Table 1 below.

TABLE 1

Doped Metal Oxide Layer

| Example | $1^{st}$ Metal Oxide (weight %) | $2^{nd}$ Metal Oxide (weight %) |
|---|---|---|
| 1. | 50 | 50 |
| 2. | 55 | 45 |
| 3. | 60 | 40 |
| 4. | 65 | 35 |
| 5. | 70 | 30 |
| 6. | 75 | 25 |
| 7. | 80 | 20 |
| 8. | 85 | 15 |
| 9. | 90 | 10 |
| 10. | 95 | 5 |
| 11. | 96 | 4 |
| 12. | 97 | 3 |
| 13. | 98 | 2 |
| 14. | 99 | 1 |

Example 3

FIG. 3 shows a floating sensor or membrane of the present invention having Pt electrodes, a Pt heater, $SiO_2/Si/SiO_2$ connectors, and a $SnO_2$—$TiO_2$ doped, metal oxide layer (dual oxide in the figure). Examples of the weight percentages of the $SnO_2$—$TiO_2$ layer shown in FIG. 3 are shown in Table 2 below.

TABLE 2

$SnO_2$—$TiO_2$ Layers

| Example | $SnO_2$ (weight %) | $TiO_2$ (weight %) |
|---|---|---|
| 1. | 50 | 50 |
| 2. | 55 | 45 |
| 3. | 60 | 40 |
| 4. | 65 | 35 |
| 5. | 70 | 30 |
| 6. | 75 | 25 |
| 7. | 80 | 20 |
| 8. | 85 | 15 |
| 9. | 90 | 10 |
| 10. | 95 | 5 |
| 11. | 96 | 4 |
| 12. | 97 | 3 |
| 13. | 98 | 2 |
| 14. | 99 | 1 |

Numerous modifications and variations of the present invention are possible in light of the above teachings. It is therefore to be understood that within the scope of the appended claims, the invention may be practiced otherwise that as specifically described herein.

We claim:

1. A chemical sensor platform, comprising:
   (a) a floating, oxidized silicon membrane, comprising: a silicon (Si) layer and a silicon oxide ($SiO_2$) layer, wherein the $SiO_2$ layer is located on top of the silicon layer and, comprises: a plurality of separate sensor areas;
   (b) at least one heating element in contact with the $SiO_2$ layer and located near at least one edge of each sensor area;
   (c) a plurality of electrical leads, each in contact with the $SiO_2$ layer, wherein one pair of electrical leads is at least partly located on each of the separate sensor areas;
   (d) a plurality of doped, metal oxide layers, wherein one doped, metal oxide layer is located on each of the plurality of sensor areas and is in contact with at least a part of the pair of electrical leads located on the same area, wherein each doped, metal oxide layer, comprises:
      (i.) a first metal oxide; and,
      (ii.) a second metal oxide; and,
   (e) a plurality of $Si/SiO_2$ connectors that are substantially isolated from the floating membrane.

2. The chemical sensor platform of claim 1, wherein there are four $Si/SiO_2$ connectors.

3. The chemical sensor platform of claim 1, wherein each first metal oxide is tin oxide ($SnO_2$).

4. The chemical sensor platform of claim 1, wherein each second metal oxide is titanium oxide ($TiO_2$).

5. The chemical sensor platform of claim 1, wherein the doped, metal oxide layer is about five to forty nanometers thick.

6. The chemical sensor platform of claim 1, wherein the weight percentage of each first metal oxide is from fifty to ninety nine percent and the weight percentage of the second metal oxide is from one to fifty percent.

7. The chemical sensor platform of claim 1, wherein there are four separate sensor areas, one heating element, four pairs of electrical leads, and four doped, metal oxide layers.

8. The chemical sensor platform of claim 1, wherein there are four separate sensor areas, one platinum (Pt) heating element, four pairs of Pt electrical leads, and four $SnO_2/TiO_2$ metal oxide layers.

9. The chemical sensor platform of claim 1, wherein there are four separate sensor areas, one Pt heating element, four pairs of Pt electrical leads, four $SnO_2/TiO_2$ metal oxide layers, and four $SiO_2/Si/SiO_2$ connectors.

10. The chemical sensor platform of claim 1, wherein there are four separate sensor areas, one Pt/titanium (Ti) heating element, four pairs of Pt/Ti electrical leads, four $SnO_2/TiO_2$ metal oxide layers, and four $SiO_2/Si/SiO_2$ connectors.

11. The chemical sensor platform of claim 1, wherein each first metal oxide is $SnO_2$ and each second metal oxide is $TiO_2$.

12. The chemical sensor platform of claim 1, wherein there is one heating element.

13. The chemical sensor platform of claim 1, wherein there is one Pt heating element.

14. The chemical sensor platform of claim 1, wherein there is one Pt/Ti heating element.

15. The chemical sensor platform of claim 1, wherein each first metal oxide is $SnO_2$, each second metal oxide is $TiO_2$, and there is one heating element.

16. The chemical sensor platform of claim 1, wherein each first metal oxide is $SnO_2$, each second metal oxide is $TiO_2$, and there is one Pt heating element.

17. The chemical sensor platform of claim 1, wherein each first metal oxide is $SnO_2$, each second metal oxide is $TiO_2$, and there is one Pt/Ti heating element.

18. The chemical sensor platform of claim 1, wherein there are four separate sensor areas, one Pt heating element, four pairs of Pt electrical leads, four $SnO_2/TiO_2$ metal oxide layers, and four $Si/SiO_2$ connectors.

19. The chemical sensor platform of claim 1, wherein there are four separate sensor areas, one Pt/Ti heating element, four pairs of Pt electrical leads, four $SnO_2/TiO_2$ metal oxide layers, and four $Si/SiO_2$ connectors.

* * * * *